US011116554B2

(12) United States Patent
Bell et al.

(10) Patent No.: US 11,116,554 B2
(45) Date of Patent: Sep. 14, 2021

(54) IMPLANTABLE BONE ADJUSTMENT DEVICE WITH IMPROVED STRENGTH

(71) Applicants: Smith & Nephew, Inc., Memphis, TN (US); Smith & Nephew Orthopaedics AG, Baar (CH); Smith & Nephew Pte. Limited, Singapore (SG)

(72) Inventors: Paul Bell, Cordova, TN (US); Haden Janda, Cordova, TN (US)

(73) Assignees: Smith & Nephew, Inc., Memphis, TN (US); Smith & Nephew Orthopaedics AG, Zug (CH); Smith & Nephew Pte. Limited, Singapore (SG)

( * ) Notice: Subject to any disclaimer, the term of this patent is extended or adjusted under 35 U.S.C. 154(b) by 75 days.

(21) Appl. No.: 16/540,223

(22) Filed: Aug. 14, 2019

(65) Prior Publication Data

US 2020/0054370 A1    Feb. 20, 2020

Related U.S. Application Data

(60) Provisional application No. 62/718,623, filed on Aug. 14, 2018.

(51) Int. Cl.
*A61B 17/72* (2006.01)

(52) U.S. Cl.
CPC .................................. *A61B 17/7216* (2013.01)

(58) Field of Classification Search
CPC . A61B 17/7216; A61B 17/7225; A61B 17/72; A61B 17/7016; A61B 17/7014; A61B 17/7017
See application file for complete search history.

(56) References Cited

U.S. PATENT DOCUMENTS

| 8,777,947 B2 | 7/2014 | Zahrly et al. |
| 9,421,046 B2 | 8/2016 | Pool et al. |
| 10,722,278 B2 | 7/2020 | Janda et al. |
| 2009/0254088 A1* | 10/2009 | Soubeiran .......... A61B 17/7216 606/63 |

(Continued)

FOREIGN PATENT DOCUMENTS

| WO | 2006079184 A1 | 8/2006 |
| WO | 2008129995 A1 | 10/2008 |

*Primary Examiner* — Julianna N Harvey
(74) *Attorney, Agent, or Firm* — Kacvinsky Daisak Bluni PLLC (57) ABSTRACT

A reconfigurable bone adjustment device includes a first member configured for attachment to a first bone fragment, a second member configured for attachment to a second bone fragment, the second member including an elongated slot formed therein; a drive mechanism configured to move the second member relative to the first member; a threaded block fixedly coupled to the first member, the threaded block positioned within the elongated slot; and a threaded rod having a proximal end operatively coupled to the drive mechanism, an intermediate portion threadably coupled to the threaded block, and a distal end operatively coupled to the second member so that rotation of the drive mechanism rotates the threaded rod and moves the second member relative to the first member. The second member being adapted and configured to provide increased strength so that the device can withstand increased patient weight bearing.

12 Claims, 8 Drawing Sheets

(56) References Cited

U.S. PATENT DOCUMENTS

| | | | |
|---|---|---|---|
| 2010/0049204 A1* | 2/2010 | Soubeiran | A61B 17/7016 |
| | | | 606/90 |
| 2011/0238126 A1* | 9/2011 | Soubeiran | A61B 17/7216 |
| | | | 606/86 R |
| 2013/0338713 A1* | 12/2013 | Kawakami | A61B 17/7014 |
| | | | 606/258 |
| 2015/0032109 A1* | 1/2015 | Pool | A61B 17/8872 |
| | | | 606/63 |
| 2019/0326043 A1 | 10/2019 | Janna et al. | |
| 2019/0336183 A1 | 11/2019 | Farley et al. | |
| 2020/0022741 A1 | 1/2020 | Janda et al. | |

* cited by examiner

IMPLANTABLE BONE ADJUSTMENT DEVICE WITH IMPROVED STRENGTH

CROSS-REFERENCE TO RELATED APPLICATION

This application claims the benefit of U.S. Provisional Patent Application Ser. No. 62/718,623, filed Aug. 14, 2018, entitled "Implantable Bone Adjustment Device with Improved Strength," the entire contents of which application is hereby incorporated by reference in its entirety.

TECHNICAL FIELD

The present disclosure generally relates to implantable reconfigurable bone adjustment devices such as, for example, intramedullary limb lengthening nails, and more particularly, but not exclusively, relates to implantable reconfigurable bone adjustment devices that have increased strength.

BACKGROUND

Implantable reconfigurable bone adjustment devices are occasionally used in orthopedic procedures to gradually adjust the position, orientation, geometry and/or length of a bone, such as, for example, by distraction, compression, realignment or bone transport. One form of an implantable reconfigurable bone adjustment device is a limb lengthening nail (LLN) configured for implantation in the medullary canal of a long bone and subsequently manipulated to adjust the length of the bone. Another form of an implantable reconfigurable bone adjustment device is a bone transport nail configured for implantation in the medullary canal of a long bone and subsequently manipulated to move a middle bone fragment across a gap between proximal and distal bone fragments to induce bone regeneration in the gap. Still other forms of implantable reconfigurable bone adjustment devices include spinal adjustment implants and implants configured to achieve other gradual adjustments to the shape, position or length of skeletal structures.

Implantable reconfigurable bone adjustment devices may include a drive mechanism including a driver such as, for example, internal magnets that are configured to rotate upon actuation by an external actuating device such as, for example, an external magnet, thereby driving a threaded rod that engages other device components to achieve a dimensional modification of the device or other relational modification between components of the device. Such dimensional modification or relational modification of the device operate on bone segments, portions or fragments to which the device is affixed to exert pressures on the bone segments, portions or fragments to which the device is affixed, thereby gradually moving the bone segments, portions or fragments relative to one another. Such devices may include a first member configured to be affixed to a first bone segment, portion or fragment; a second member configured to be affixed to another bone segment, portion or fragment; a rod with at least one thread, the rotation of which causes displacement of the second member relative to the first member, and a drive mechanism for controlling the rotation of the threaded rod. In the case of certain LLN devices, for example, the second member may be assembled telescopically relative to the first member and rotation of the threaded rod operates to telescopically displace the second member relative to the first member, thereby increasing the distance between the bone segments, portions or fragments to which the first member and the second member are respectively affixed.

While currently-available bone adjustment devices have produced excellent results, many of these devices exhibit one or more shortcomings or disadvantages that render the device susceptible to failure. For example, one common drawback associated with implantable reconfigurable bone adjustment devices (e.g., LLN nails) is their reduced or limited weight-bearing capability. That is, for example, LLN nails are telescopic in nature and thus weaker than a tradition intramedullary nail used in trauma applications. For these reasons among others, a need remains for further improvements in this technological field. The present disclosure addresses this need.

SUMMARY

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides a reconfigurable bone adjustment device comprising: a first member configured for attachment to a first bone fragment; a second member configured for attachment to a second bone fragment, the second member including a circumferential outer surface and an elongated slot formed in the circumferential outer surface; a drive mechanism configured to move the second member relative to the first member; a threaded block fixedly coupled to the first member, the threaded block positioned within the elongated slot; and a threaded rod having a proximal end operatively coupled to the drive mechanism, an intermediate portion threadably coupled to the threaded block, and a distal end operatively coupled to the second member so that operation of the drive mechanism rotates the threaded rod and moves the second member relative to the first member; wherein the circumferential outer surface includes a first side surface and a diametrically opposed second side surface, the elongated slot is formed in the first side surface only.

In some embodiments, the elongated slot does not extend completely through the second member to the second side surface.

In some embodiments, the elongated slot is a partial slot formed in the circumferential outer surface of the second member, the partial slot does not extend completely through the second member. In some embodiments, the second side surface opposite the elongated slot formed in the first side surface is solid.

In some embodiments, the threaded block includes a first end and a second end, the first end being at least partially disposed in the elongated slot, the first end of the threaded block being welded to the first member.

In some embodiments, the second end of the threaded block is completely devoid of any welding to the first member.

In some embodiments, a portion of a circumferential outer surface of the first member positioned between the threaded block and a distal end of the first member is devoid of any slot.

In some embodiments, the first end of the threaded block is welded to the first member via a weld that completely surrounds the first end of the threaded block.

In some embodiments, the second end of the threaded block contacts an inner surface of the second member such that deflection of the threaded block is reduced.

In some embodiments, the slot and the threaded block include a wedge or taper shape.

In some embodiments, the threaded block includes first and second, non-parallel side surfaces.

In some embodiments, the elongated slot defines first and second walls in the second member, the first and second wall being non-parallel relative to each other.

The present disclosure also provides a reconfigurable bone adjustment device comprising: a first member configured for attachment to a first bone fragment; a second member configured for attachment to a second bone fragment, the second member including an elongated slot; a drive mechanism configured to move the second member relative to the first member; a threaded block fixedly coupled to the first member, the threaded block positioned within the elongated slot; and a threaded rod having a proximal end operatively coupled to the drive mechanism, an intermediate portion threadably coupled to the threaded block, and a distal end operatively coupled to the second member so that rotation of the drive mechanism rotates the threaded rod and moves the second member relative to the first member; wherein the elongated slot formed in the second member is a thru slot extending from a first circumferential surface of the second member to a second, diametrically opposed circumferential surface of the second member, the thru-slot having an asymmetric design.

In some embodiments, a width of the slot in the first circumferential surface is greater than a width of the slot in the second circumferential surface.

In some embodiments, the width of the slot in the first circumferential surface is 3 mm and the width of the slot in the second circumferential surface is 1½ mm.

Embodiments of the present disclosure provide numerous advantages. For example, by incorporating, providing, etc. a partial slot or smaller slot design, the reconfigurable bone adjustment device is capable of withstanding greater weight bearing.

Further features and advantages of at least some of the embodiments of the present invention, as well as the structure and operation of various embodiments of the present invention, are described in detail below with reference to the accompanying drawings.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein.

DETAILED DESCRIPTION

For the purposes of promoting an understanding of the principles of the present disclosure, reference will now be made to the embodiments illustrated in the figures and specific language will be used to describe the same. It will nevertheless be understood that no limitation of the scope of the disclosure is thereby intended. Any alterations and further modifications in the described embodiments, and any further applications of the principles of the present disclosure as described herein are contemplated as would normally occur to one skilled in the art to which the disclosure relates.

Various implantable reconfigurable bone adjustment devices are disclosed herein. In one embodiment, the implantable reconfigurable bone adjustment device may include a first member, body portion or component (used interchangeably herein without the intent to limit), a second member, and a rotatable threaded rod that engages at least one component affixed to the first member and at least one component operable to axially move the second member relative to the first member. The implantable reconfigurable bone adjustment device may also include a drive mechanism to controllably actuate rotation of the threaded rod. In certain embodiments, the drive mechanism may be an internal magnet coupled to the threaded rod such that rotation of the internal magnet drives rotation of the threaded rod. This can be achieved, for example, by fixing the threaded rod directly to the internal magnet or a housing in which the internal magnet is contained or can be achieved by connecting the threaded rod indirectly to the internal magnet, such as through a gear mechanism or other structure positioned therebetween. As described further herein, torque may be applied to the internal magnet by applying a rotating magnetic field across the internal magnet from an external source. In other implantable reconfigurable bone adjustment device embodiments, rotation of the threaded rod may be controlled or driven by a drive mechanism other than an internal magnet. Alternative drive mechanisms for driving the threaded rod may include any other now known or hereafter developed drive mechanisms known to a person of ordinary skill in the art, including, for example, an electric motor with or without gear reduction, a current source inside or outside the patient's body, a permanent magnet with a gear reducer and a rotating magnetic field source external to the patient, etc. In alternate embodiments, the drive mechanism can be configured to drive the threaded rod in one direction only, or in both directions, according to requirements. The first and second body portions are dimensioned such that the body portions can move in at least one axial direction with respect to one another upon rotation of the threaded rod. For additional information on the components, operation, features, etc. of various representative, but non-limiting, examples of implantable reconfigurable bone adjustment devices contemplated by the present disclosure reference is hereby made to U.S. patent application Ser. No. 16/473,961 entitled Bone Transport Nail; Ser. No. 16/473,942 entitled Actuation System and Method for Orthopedic Implants with a Rotatable Internal Magnet; Ser. No. 16/142,269 entitled Implantable Bone Adjustment Devices; and PCT international Patent Application No. PCT/US18/15731 entitled Implantable Bone Adjustment Devices, the contents of each application is hereby incorporated by reference in its entirety.

One representative, but non-limiting, example of an implantable reconfigurable bone adjustment device contemplated by the present disclosure is an intramedullary limb lengthening nail, such as intramedullary ("IM") limb lengthening nail 101 depicted in FIGS. 1-4. Further details regarding representative IM limb lengthening nails are available in U.S. Pat. No. 8,777,947, which is hereby incorporated herein by reference in its entirety. Referring to FIGS. 1-4, the IM limb lengthening nail 101 may include a proximal body portion 110, a distal body portion 130, and a threaded rod 170 operatively associated with the proximal body portion 110 and the distal body portion 130. In use, rotation of the threaded rod 170 causes the proximal body portion 110 and the distal body portion 130 to move with respect to one another. In one embodiment, as will be described in greater detail, the proximal body portion 110 may be configured as an outer body and the distal body portion 130 may be configured as an inner body so that at least a portion of the distal body portion 130 may be received within the proximal body portion 110. Alternatively, it is envisioned that the proximal body portion 110 may be configured as the inner body and the distal body portion 130 may be configured as the outer body. In one embodiment, the threaded rod 170 may be mounted in and coupled to the distal body portion 130.

Each of the proximal body portion 110, distal body portion 130, and threaded rod 170 has a proximal end 111, 131, 171 and a distal end 114, 134, 174, respectively. The IM limb lengthening nail 101 may also include a drive mechanism for driving rotation of the threaded rod 170. In use, actuation of the drive mechanism is controlled to achieve a desired amount of rotation over time and at a desired rate, thereby achieving a desired amount of bone adjustment at a desired rate. In certain devices, the drive mechanism includes a magnet hermetically sealed in a housing, although other types of drive mechanisms, such as electric motors, are contemplated. That is, the IM limb lengthening nail 101 includes an inner magnet 150 (also referred to herein as "internal magnet") seated in the proximal body portion 110 and coupled, either directly or indirectly, to the proximal end 171 of the threaded rod 170. A distal end 174 of the threaded rod 170 may be coupled to a distal block 136, which is coupled to the distal body portion 130. The IM limb lengthening nail 101 may also include a threaded block 119 (FIG. 4) coupled to the proximal body portion 110 and engaged with the threaded rod 170.

The term "inner" or "internal" is used herein in reference to the magnet 150 positioned within the implantable reconfigurable bone adjustment device 101 to distinguish this magnet from a different magnet or multiple different magnets employed by an external actuator as described in greater detail below, which magnet or magnets of an external actuator, are referred to as "outer magnets." While neodymium magnets are suggested, other magnets may be employed as will be apparent to those skilled in the art.

In use, the distal body portion 130 includes an elongated slot 140 which enables the threaded block 119 to slide along the distal body portion 130 during relative movement of the proximal and distal body portions 110, 130 along the longitudinal axis 190. That is, as will be described in greater detail below, the threaded rod 170 is threadably coupled to the threaded block 119, which is fixedly coupled to the proximal body portion 110 (e.g., the threaded block 119 may be, for example, laser welded to the proximal body portion 110). Thus, in use, rotation of the internal magnet 150 causes the threaded rod 170 to rotate, which causes the distal body portion 130 to move relative to the proximal body portion 110. As the distal body portion 130 moves relative to the proximal body portion 110, the slot 140 formed in the distal body portion 130 moves relative to the threaded block 119. It should be appreciated that this is but one example embodiment, other embodiments are envisioned, so long as operation of the drive mechanism moves the proximal and distal body portions 110, 130 relative to each other.

The proximal body portion 110 may be at least partially hollow, having an inner wall 120 that defines an internal cylindrical chamber, for accommodating a portion of the distal body portion 130, which extends through the distal end 114 of the proximal body portion 110. The proximal and distal body portions 110, 130 are dimensioned such that the proximal and distal body portions 110, 130 can move in both axial directions with respect to one another. The proximal body portion 110 may also house the inner magnet 150, which may be mounted in a housing or carrier to facilitate the coupling of the inner magnet 150 to the threaded rod 170. The inner magnet 150 may include at least one permanent magnet, one of the poles of which is directed in one radial direction relative to a longitudinal axis 190 of the IM limb lengthening nail 101 and the other pole directed in an opposite radial direction relative to the longitudinal axis 190. As will be appreciated by one of ordinary skill in the art, the inner magnet 150 may be rotated about the longitudinal axis 190 of the IM limb lengthening nail 101 by application of an externally applied rotating magnetic field. The IM limb lengthening nail 101 may also include a first locking portion 112 and a second locking portion 132, each of which includes a plurality of fastener openings 113, 133 structured to receive fasteners for coupling the respective ends of the IM limb lengthening nail 101 to the patient's bone.

The inner magnet 150 is coupled, either directly or indirectly, to the threaded rod 170, which extends through the proximal end 131 of the distal body portion 130. The threaded rod 170 may also extend through a bearing (not shown) which engages the inner wall 120 of the proximal body portion 110. Similarly, a bearing may be coupled to a proximal end of the inner magnet 150 to facilitate rotation of the inner magnet 150 within the proximal body portion 110. The distal end 174 of the threaded rod 170 is engaged with the distal block 136, which is coupled to the distal body portion 130. In use, the distal block 136 permits rotation of the threaded rod 170 with respect to the distal body portion 130 and couples the distal body portion 130 and the threaded rod 170 for joint movement along the longitudinal axis 190. For example, the distal block 136 may be coupled or affixed to the distal body portion 130 such that the threaded rod 170 can rotate freely without altering the position of the distal end 174 of the threaded rod 170 with respect to the distal body portion 130. The threaded rod 170 also extends through the threaded block 119, which is coupled to the proximal body portion 110.

The threaded rod 170 may include a set of external threads which engage with a set of internal threads formed in a threaded bore 121 (FIG. 4) formed in the threaded block 119. As noted above, the threaded rod 170 is axially coupled to the distal body portion 130 via the distal block 136 and is axially and rotationally coupled to the inner magnet 150. In addition, the threaded rod 170 is threadably engaged with the threaded block 119, which is axially and rotationally coupled to the proximal body portion 110. As a result, rotation of the inner magnet 150 causes relative movement of the proximal and distal body portions 110, 130 along the longitudinal axis 190. Once again, it should be appreciated that this is but one example embodiment, other embodiments are envisioned, so long as operation of the drive mechanism moves the proximal and distal body portions 110, 130 relative to each other.

Figure 1:
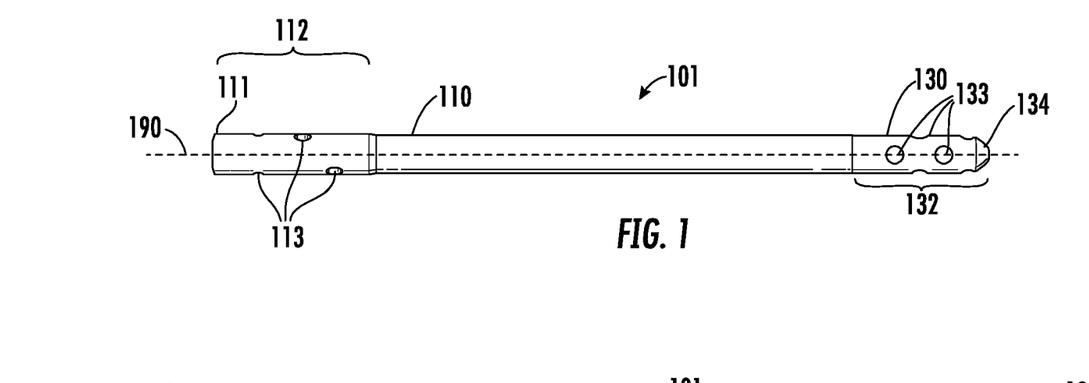
FIG. 1 illustrates a side view of an example of an embodiment of an intramedullary limb lengthening nail, the limb lengthening nail illustrated in a retracted or contracted state.
Figure 2:
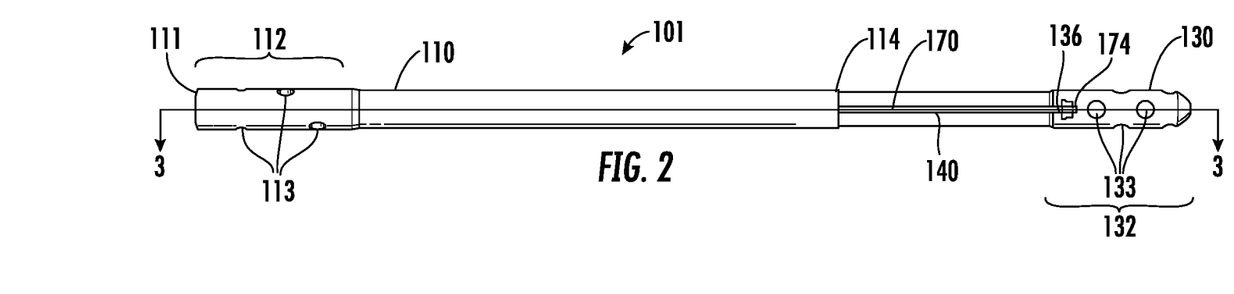
FIG. 2 illustrates a side view of the intramedullary limb lengthening nail shown in FIG. 1, the limb lengthening nail illustrated in an extended or distracted state.
Figure 3:
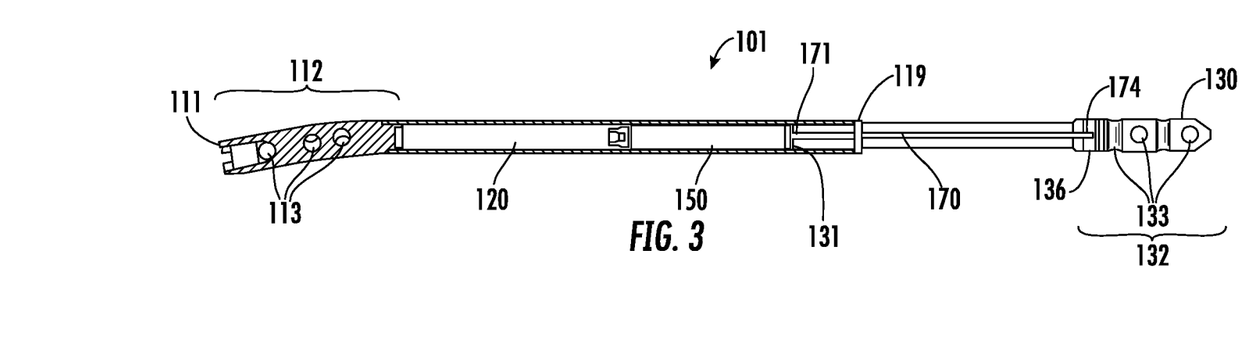
FIG. 3 illustrates a cross-sectional view of the limb lengthening nail shown in FIG. 2, taken along line 3-3.
Figure 4:
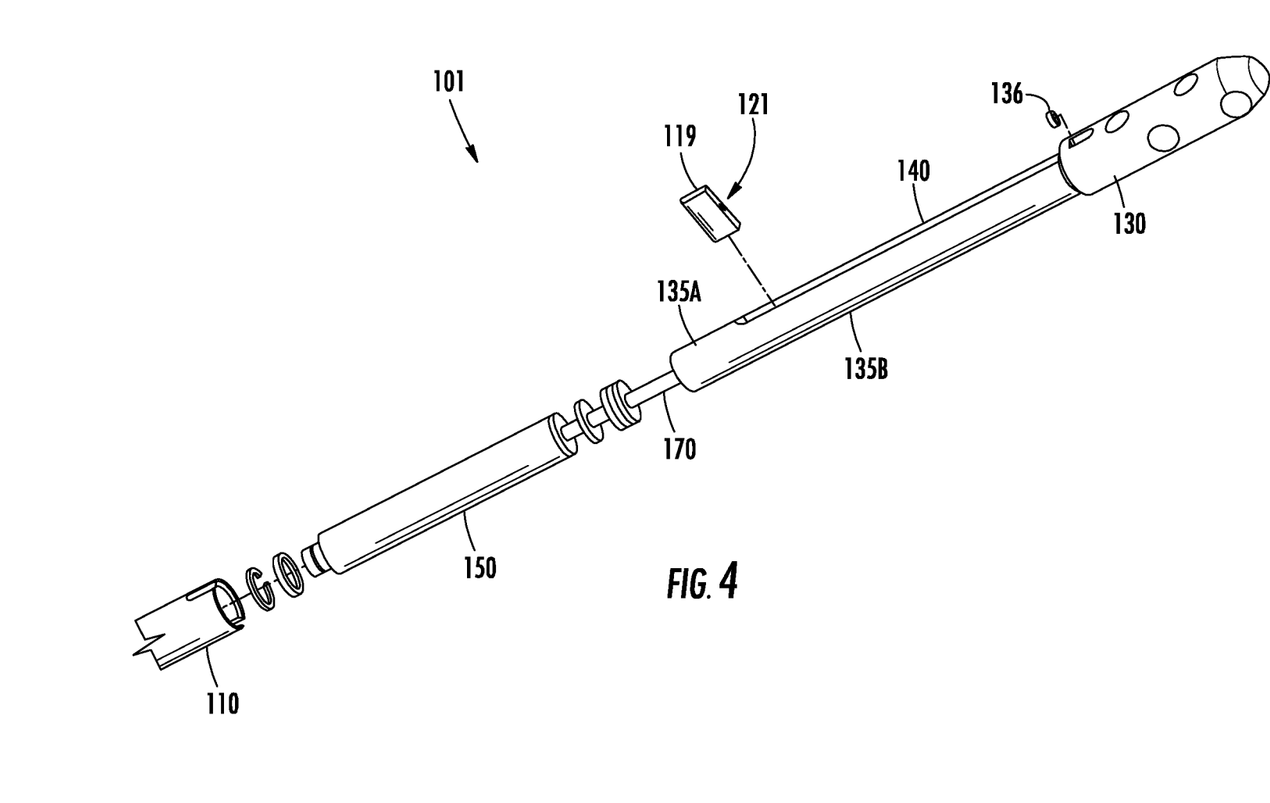
FIG. 4 illustrates a partially, exploded view of an example of an embodiment of an intramedullary limb lengthening nail.

FIG. 1 illustrates the IM limb lengthening nail 101 in a retracted or contracted state, and FIGS. 2 and 3 illustrate the IM limb lengthening nail 101 in an extended or distracted state. The IM limb lengthening nail 101 may be moved between the contracted and distracted states by rotating the inner magnet 150 by application of an externally applied rotating magnetic field. More specifically, rotation of the inner magnet 150 may cause rotation of the threaded rod 170 resulting in movement of the distal body portion 130 relative to the proximal body portion 110 along the longitudinal axis 190, thereby adjusting the length of the IM limb lengthening nail 101. As is evident from a comparison of FIGS. 2 and 3, the longitudinal positions of the distal block 136 and the distal end 174 of the threaded rod 170 with respect to the distal body portion 130 remain unchanged. That is, the elongated slot 140 formed in the distal body portion 130 enables the threaded block 119 to slide along the distal body portion 130 during relative movement of the proximal and distal body portions 110, 130 along the longitudinal axis 190.

In use, the IM limb lengthening nail 101 is configured for implantation in a bone having a medullary canal. Typically, the IM limb lengthening nail 101 is implanted such that the first locking portion 112 is affixed to a first bone portion and the second locking portion 132 is affixed to a second bone portion, and a gap separates the first and second bone portions. The gap may be formed, for example, during an osteotomy procedure in which the bone is severed for purposes of lengthening the bone over time. The IM limb lengthening nail 101 is implanted into the medullary canal of the bone and is surgically coupled to the bone. For example, the proximal body portion 110 is coupled to the first bone portion and the distal body portion 130 is coupled to the second bone portion by fasteners such as screws or pins, which may be received in or otherwise engaged with the openings 113, 133.

Both distraction and compaction of the proximal and distal body portions 110, 130 with respect to each other is possible. Thus, with the IM limb lengthening nail 101 implanted in the bone, the segmented portions of the bone may be distracted or compacted as necessary by rotation of the threaded rod 170 and the inner magnet 150 in a first direction or a second direction, respectively, thereby enabling lengthening or shortening of the bone. In other words, the telescoping ability allows the IM limb lengthening nail 101 to both distract and contract the bone portions, to which the proximal and distal body portions 110, 130 are coupled. During lengthening, the IM limb lengthening nail 101 may be transitioned from the retracted state (FIG. 1) to the expanded state (FIG. 2), thereby lengthening the bone. The IM limb lengthening nail may be transitioned from the retracted state to the expanded state gradually over a given period of time, such that an ossified region forms as the bone lengthens and heals.

It should be understood that the principles and features of the present disclosure are not limited to use with the IM limb lengthening nail illustrated and described in connection with FIGS. 1-4 and that the principles and features of the present disclosure may be used in combination with other implantable reconfigurable bone adjustment devices such as, for example, other limb lengthening devices, an IM bone transport nail, or the like. In addition, it is to be understood that the present disclosure in not limited to use with in an implantable reconfigurable bone adjustment device, it being understood that the principles and features of the present disclosure find advantageous use with a variety of other reconfigurable bone adjustment devices that include a drive mechanism operable to controllably rotate a driver that is coupled to a threaded rod to drive rotation of the threaded rod to move first and second members of the device relative to one another.

In one example embodiment, as will be readily appreciated by one of ordinary skill in the art, during operation, as indicated above, to rotate the threaded rod 170, a rotating magnetic field is applied to the device 101 to apply torque to the internal magnet 150. In one embodiment, this torque is applied by magnetically coupling an external magnetic actuator with the internal magnet 150.

The creation of a magnetic driving field for rotating the internal magnet 150 and the threaded rod 170 coupled coaxially therewith can be accomplished by a wide variety of mechanisms. In one manner of actuating rotation of the internal magnet 150 following implantation of an implantable reconfigurable bone adjustment device 101 in a skeletal position of a patient, an external magnetic actuator, also referred to herein as an actuation unit may be used. In one embodiment, the external magnetic actuator is operable to position a driving magnet, also referred to herein as an outer magnet, near the implanted device 101, but external to the patient, at the height of the internal magnet 150. The external magnetic actuators are designed and positioned to maximize torque to the internal magnet 150 and the threaded rod 170 and, in any event, to provide sufficient torque to rotate the internal magnet 150 despite the distance between the internal magnet 150 and the one or more outer magnets in the external magnetic actuator and applied resisting forces on the device 101. In this regard, rotation of the internal magnet 150 must overcome any compressive load imparted between the components of the device 101 by bone tissue and other tissues of the patient, together with internal frictional forces of the device 101.

In the presence of a magnetic driving field perpendicular to the rotational axis of the internal magnet 150 (which lies on the longitudinal axis 190 in the respective embodiments) and rotating around this axis, the internal magnet 150 tends to become oriented in the magnetic driving field, which applies a torque to the internal magnet 150 and causes the internal magnet 150 to rotate in the same rotational direction of the magnetic driving field, together with threaded rod 170 that is coupled coaxially with internal magnet 150, if the applied torque is greater than the load torque on threaded rod 170 under the load applied to it at the time when the magnetic driving field is activated.

In one embodiment, the driving magnet comprises at least one permanent magnet, one of the poles of which is directed towards longitudinal axis 190. In another embodiment, an even greater torque can be applied to the internal magnet 150 by using two permanent driving magnets positioned such that the south pole of one is facing the north pole of the other, and such that the implanted device and the part of the patient's body that surrounds the implanted device are positioned between the two permanent magnets.

Figure 5:
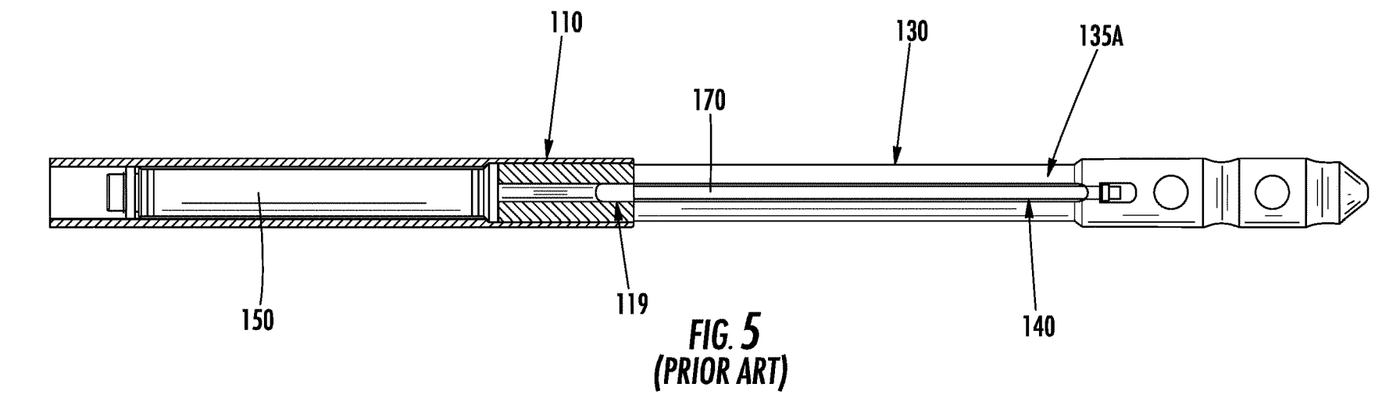
FIG. 5 illustrates a partial detailed view of a conventional limb lengthening nail.
Figure 6:
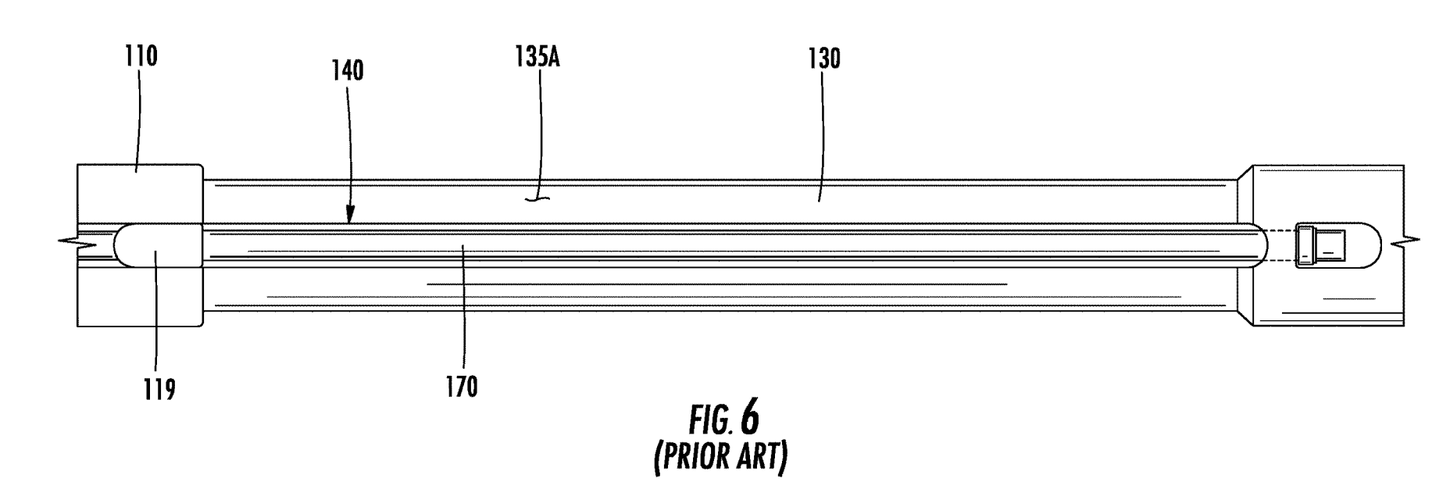
FIG. 6 illustrates an alternate, partial detailed view of the conventional limb lengthening nail shown in FIG. 5.

As previously mentioned, one common problem associated with IM limb lengthening nails is their limited or reduced weight-bearing capability. This is, in part, due to the slot 140 formed in the distal body portion 130 being in the form of a thru-slot. Referring to FIGS. 5 and 6, as illustrated in conventional, known devices, the slot 140 extends completely through the distal body portion 130 (e.g., the slot 140 extends from a first side surface 135A of the distal body portion 130 to a second side surface 135B (FIG. 4) of the distal body portion 130). While incorporation of a thru slot 140 facilitates the distal body portion 130 to move or translate relative to the proximal body portion 110 without allowing the distal body portion 130 to rotate, the thru slot 140 reduces the implantable reconfigurable bone adjustment device's ability to bear weight (e.g., the thru slot 140 weakens the overall strength of the device 101). This is especially true when the device 101 is in its fully extended position.

In accordance with one aspect of the present disclosure, the implantable reconfigurable bone adjustment device 101 is modified to provide increase overall strength of the device. That is, in accordance with one aspect of the present disclosure, the implantable reconfigurable bone adjustment device 101 is modified to provide increase weight bearing capability so that the implantable reconfigurable bone adjustment device 101 can support or nearly support full weight bearing capabilities similar to non-telescopic IM nails leading to improved patient satisfaction through the lengthening phase of treatment.

Figure 7:
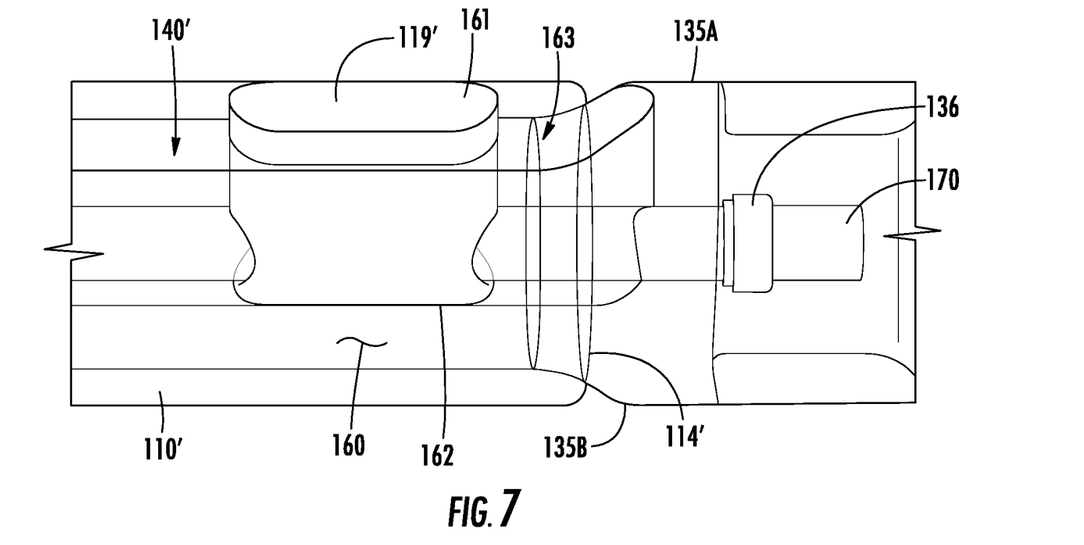
FIG. 7 illustrates a detail view of an example of an embodiment of an intramedullary limb lengthening nail in accordance with one aspect of the present disclosure, the intramedullary limb lengthening nail incorporating a partial slot design.
Figure 8:
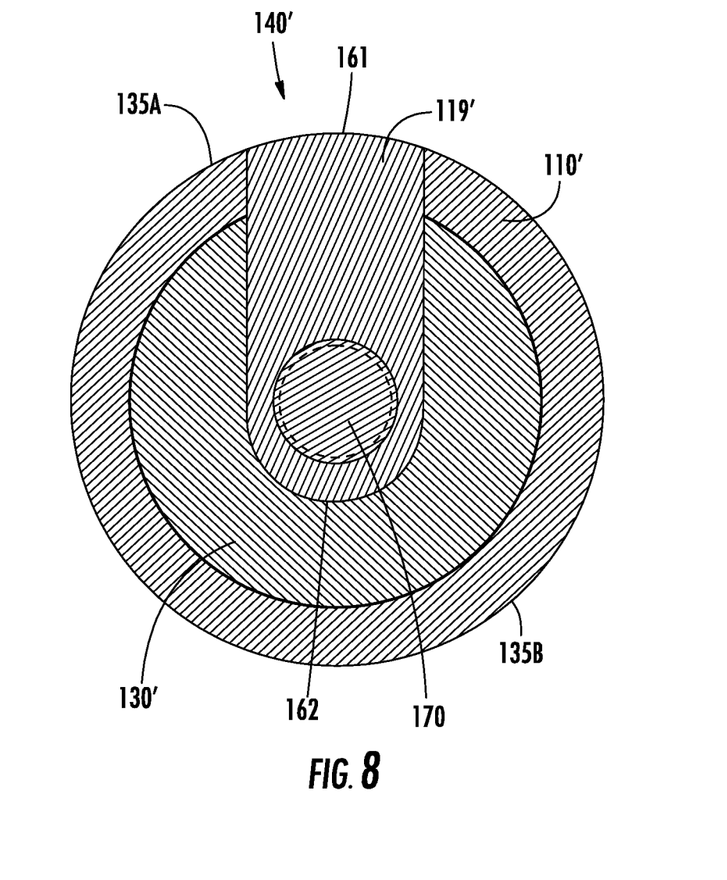
FIG. 8 is a cross-sectional view of the intramedullary limb lengthening nail shown in FIG. 7.

In accordance with one aspect of the present disclosure, the distal body portion 130 is modified to increase its strength and thus the strength of the entire device 101. Referring to FIGS. 7 and 8, in one embodiment, the slot 140' formed in the distal body portion 130' is no longer a thru slot. That is, as illustrated, the distal body portion 130' only includes a slot 140' formed in a single side surface thereof (e.g., the distal body portion 130' includes an outer circumferential surface including first and second diametrically opposed surfaces 135A, 135B, the elongated slot 140' extends thru, is formed in, etc. only one circumferential surface of the distal body portion 130' such as, for example, the first side surface 135A).

As illustrated in the illustrated example embodiment of FIGS. 7 and 8, the slot 140' formed in the distal body portion 130' is modified from a full thru slot (e.g., as used in conventional known devices illustrated in FIGS. 5 and 6) to a partial slot (e.g., the slot 140' is formed in the first side surface 135A only and does not extend completely through the distal body portion 130' to the diametrically opposed second side surface 135B). As a result, the second side surface 135B opposite of the slot 140' remains solid.

In connection with this embodiment, since the threaded block 119' no longer extends completely thru the distal body portion 130', the threaded block 119' can no longer be welded on both ends to the proximal body portion 110' (e.g., the threaded block 119' can't be welded to, along, or the like, the second side surface 135B where the elongated slot 140 is missing). Rather, the threaded block 119' can only be welded to the proximal body portion 110' to, along, or the like, on the first side surface 135A adjacent to the elongated slot 140'. That is, the threaded block 119' includes a first end 161 and a second end 162, the first end 161 being at least partially disposed, received, etc. in the elongated slot 140' formed in the first side surface 135A of the circumferential outer surface of the distal body portion 130'. The threaded block 119' is at least partially welded to the proximal body portion adjacent to, along, or the like, the first end 161 of the threaded block 119'. The second end 162 of the threaded block 119' is not welded to the proximal body portion.

In accordance with one aspect of the present disclosure, in order to strengthen the connection between the threaded block 119' and the proximal body portion 110', the threaded block 119' is fully captured within the proximal body portion 110' (e.g., a portion of the proximal body portion 110' located distally or above the threaded block 119' remains solid; a portion 163 of the circumferential outer surface of the proximal body portion 110' positioned between the threaded block 119' and the distal end 114' of the proximal body portion 110' is solid and devoid of any slot). Thus arranged, the weld between the proximal body portion 110' and the threaded block 119' can extend completely around the end of the threaded block 119' as opposed to the conventional, existing U-shaped welds. Although it is still envisioned that a U-shaped weld between the threaded block 119' and the proximal body portion 110' may be utilized to facilitate easier assembly.

Additionally, and/or alternatively, in one embodiment, the second end 162 of the threaded block 119' contacts the inner surface of the distal body portion 130' such that deflection of the threaded block 119' is reduced to reduce stress on the one-sided weld between the proximal body portion 110' and the threaded block 119'. Thus arranged, the inner wall portion 160 of the proximal body portion 110' is in contact with the second end 162 of the threaded block 119' as illustrated in FIG. 7. As necessary, any space between the second end 162 of the threaded block 119' and the inner surface of the distal body portion 130' can be built into the design. In one embodiment, the amount of contact between the second end 162 of the threaded block 119' and the inner surface of the distal body portion 130' can be controlled during assembling of the limb lengthening nail 101, for instance, during assembly, one or more shims or the like may be incorporated to keep the threaded block 119' at a desired height when the proximal body portion 110' to threaded block 119' weld is completed. Thus arranged, the shims could be used to ensure that the threaded block 119' is welded in the optimal position. Thereafter, after welding, the shims would be removed.

As illustrated in FIG. 7, the distal body portion 130' includes a partial slot design having a solid back wall surface. The threaded block 119' is welded to the proximal body portion 110' along a side thereof.

Figure 9A:
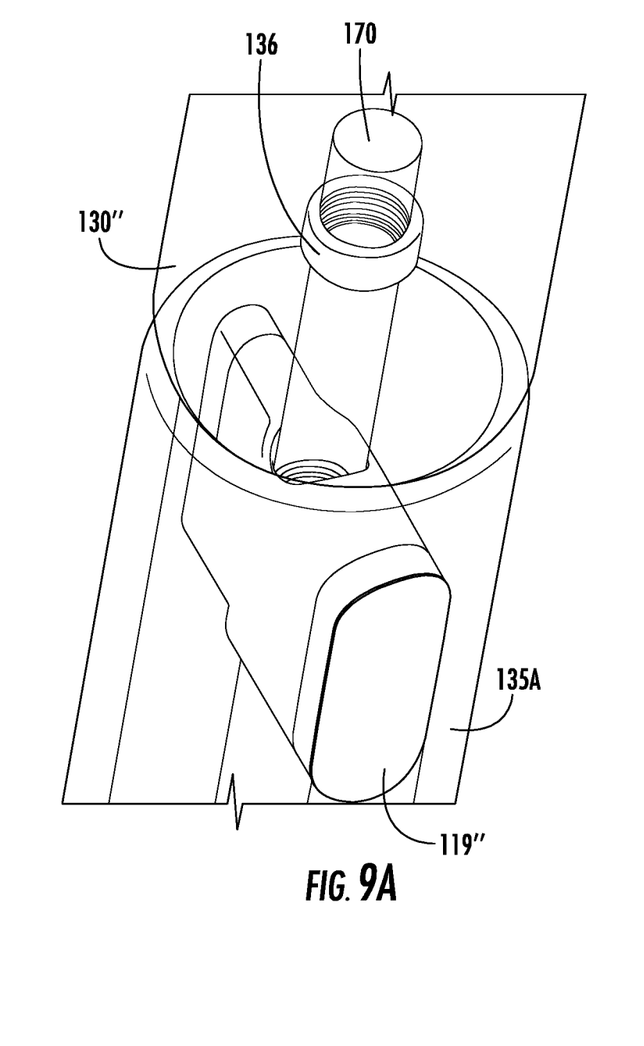
FIGS. 9A and 9B illustrate detail views of an alternate example of an embodiment of an intramedullary limb lengthening nail in accordance with one aspect of the present disclosure, the intramedullary limb lengthening nail incorporating an asymmetrical slot design.
Figure 9B:
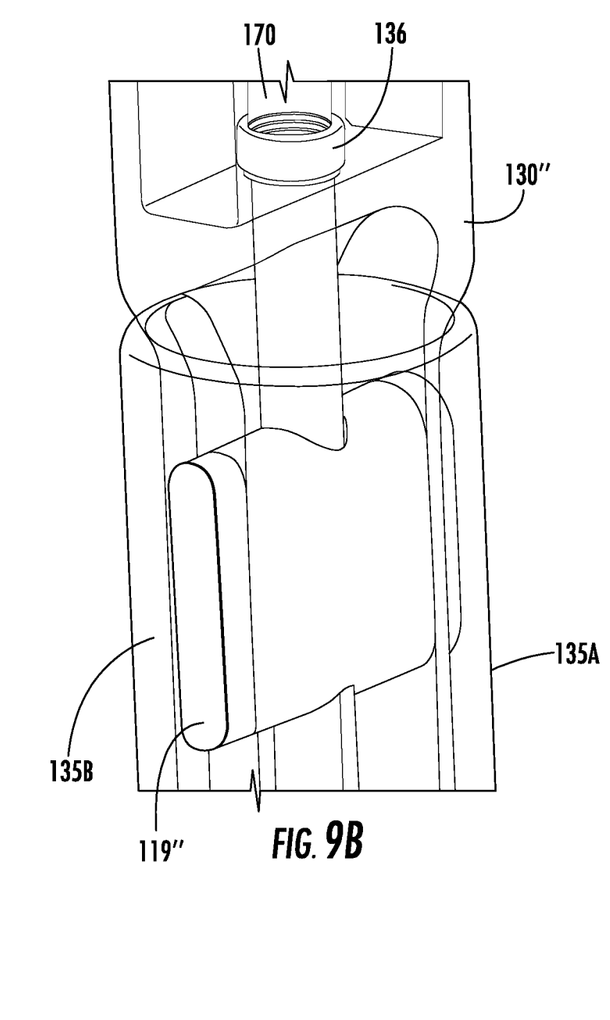
Figure 10:
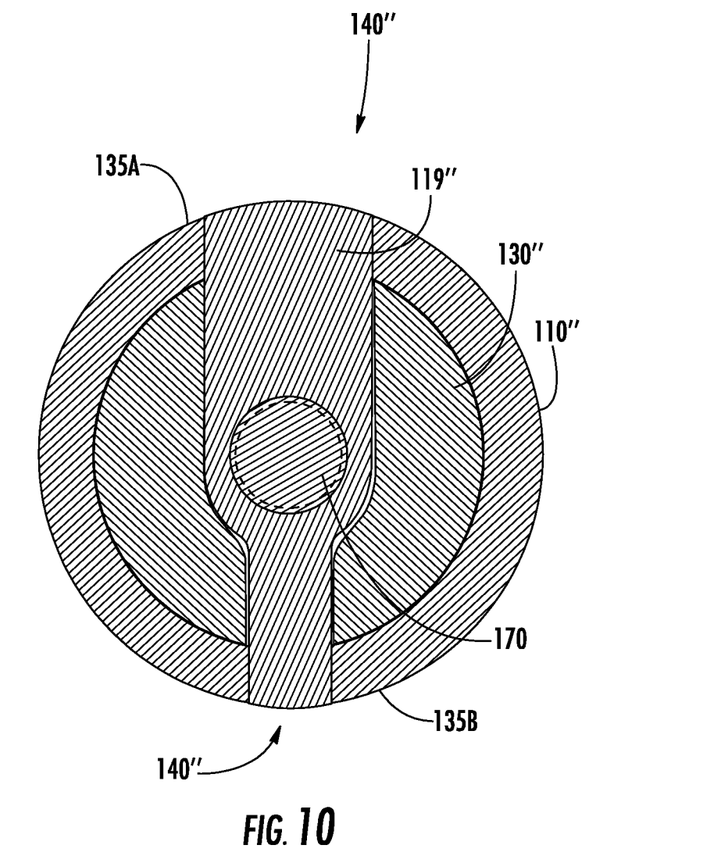
FIG. 10 is a cross-sectional view of the intramedullary limb lengthening nail shown in FIGS. 9A and 9B.

Referring to FIGS. 9A, 9B and 10, in an alternate embodiment, the slot 140" may be in the form of a thru slot (e.g., slot 140" extends from the first side surface 135A to the second side surface 135B). However, in accordance with the principles of the present disclosure, the second side surface 135B of the distal body portion 130" may include a slot width that is narrower than a slot width of the slot formed in the first side surface 135A of the distal body portion 130". By forming asymmetric slots, and thus a corresponding asymmetric threaded block 119", the overall strength of the distal body portion 130" and thus the entire implant 101 is increased. Incorporation of an asymmetric design would allow welding of the threaded block 119" to both sides of the proximal body portion 110". In one non-limiting embodiment, it is envisioned that the first slot width may be approximately 3 mm and the second slot width may be approximately 1½ mm.

Figure 11:
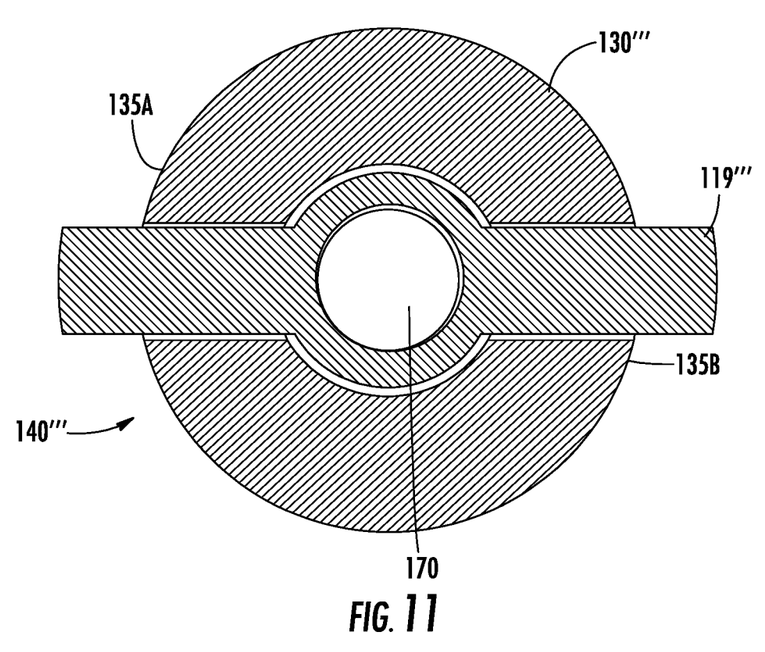
FIG. 11 is a cross-sectional view of an alternate example of an embodiment of an intramedullary limb lengthening nail in accordance with one aspect of the present disclosure, the intramedullary limb lengthening nail incorporating a smaller slot width design.

Referring to FIG. 11, in another alternative embodiment, the slot 140' may be in the form of a thru slot (e.g., slot 140''' extends from the first side surface 135A to the diametrically opposed second side surface 135B). However, in accordance with the principles of the present disclosure, both sides of the slot 140''' (e.g., portion of slot formed in the first side surface 135A and second side surface 135B) may include a smaller slot width to provide increased strength. For example, in one non-limiting embodiment, it is envisioned that the first and second slot widths may be approximately 1½ mm. In accordance with one aspect of the present embodiment, the device may also include an increased aperture to accept the threaded portion of the threaded block.

Figure 12:
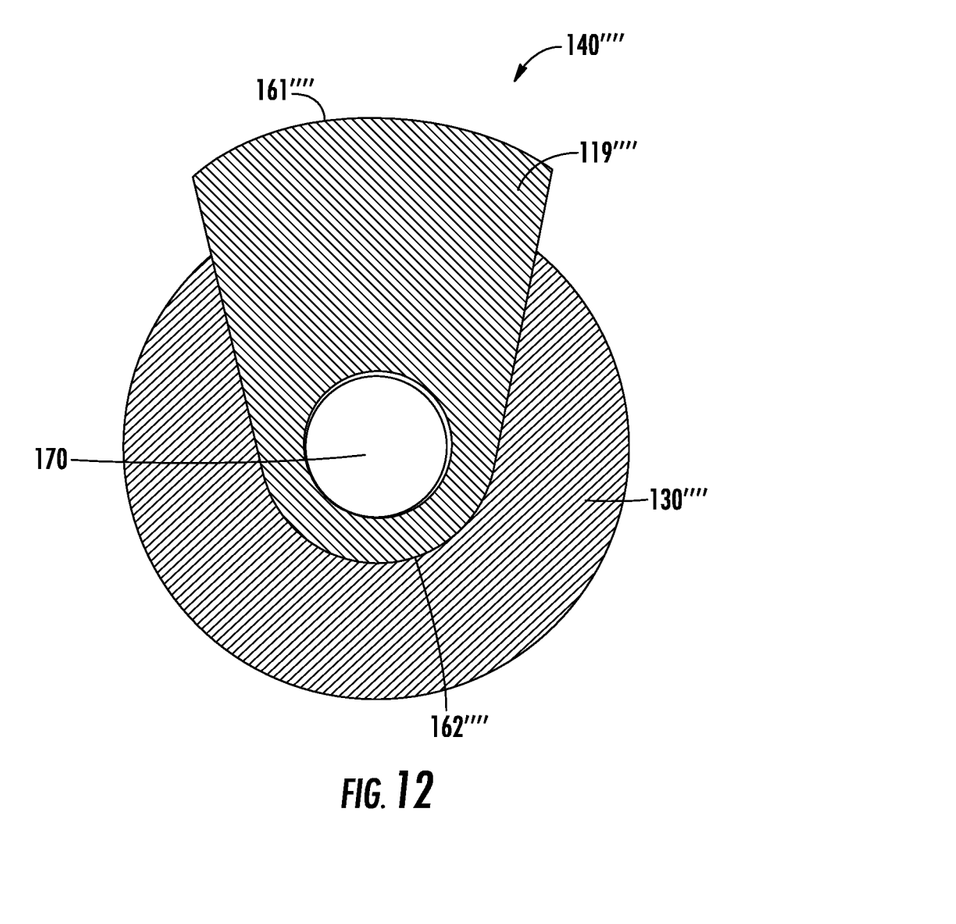
FIG. 12 is a cross-sectional view of an alternate example of an embodiment of an intramedullary limb lengthening nail in accordance with one aspect of the present disclosure, the intramedullary limb lengthening nail incorporating a wedge or taper shape slot.

Referring to FIG. 12, in another alternative embodiment, the slot 140' formed in the distal body portion 130' and the corresponding threaded block 119"" may include a partial slot design wherein the slot 140' and the threaded block 119"" have a modified shape such as, for example, a wedge or taper shape as opposed to parallel sides. By incorporating a wedge or taper shape, the walls of the slot 140"" would be angled outward allowing for more weld volume as the threaded block 119"" would be wider at the outer circumference of the proximal body portion (e.g., width of the threaded block 119"" increases as one moves from the second end 162' of the threaded block 119"" to the first end 161' of the threaded block 119"").

Orthopedic implants and prosthetics such as reconfigurable bone adjustment devices described herein typically are formed of a biocompatible metal. Medical grade cobalt-chromium (CoCr) alloys such as cobalt-chromium-molybdenum (CoCrMo) and cobalt-chromium-iron (CoCrFe) are among the most suitable metallic biomaterials, particularly for weight-bearing implants. These alloys typically exhibit high mechanical properties, adequate corrosion resistance, and acceptable biocompatibility. In one embodiment, a reconfigurable bone adjustment device according to the present disclosure is formed of a cobalt-chromium-iron (CoCrFe) alloy. In another embodiment, the alloy comprises a 40Co-20Cr-16Fe-15Ni-7Mo alloy. It should be appreciated however that the reconfigurable bone adjustment devices may be manufactured from any suitable material.

While the present disclosure has been illustrated and described in detail in the drawings and foregoing description, the same is to be considered as illustrative and not restrictive in character, it being understood that only the certain embodiments have been shown and described and that all changes, alternatives, modifications and equivalents that come within the spirit of the disclosure are desired to be protected.

It should be understood that while the use of words such as preferable, preferably, preferred or more preferred utilized in the description above indicate that the feature so described may be more desirable, it nonetheless may not be necessary and embodiments lacking the same may be contemplated as within the scope of the present disclosure, the scope being defined by the claims that follow. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A reconfigurable bone adjustment device comprising:
a first member configured for attachment to a first bone fragment;
a second member configured for attachment to a second bone fragment, the second member including a circumferential outer surface and an elongated slot formed in the circumferential outer surface;
a drive mechanism configured to move the second member relative to the first member;
a threaded block fixedly coupled to the first member, the threaded block positioned within the elongated slot; and
a threaded rod having a proximal end operatively coupled to the drive mechanism, an intermediate portion threadably coupled to the threaded block, and a distal end operatively coupled to the second member so that operation of the drive mechanism rotates the threaded rod and moves the second member relative to the first member;
wherein the circumferential outer surface includes a first side surface and a diametrically opposed second side surface, the elongated slot is formed in the first side surface only; and
wherein a portion of a circumferential outer surface of the first member positioned between the threaded block and a distal end of the first member is devoid of any slot.

2. The reconfigurable bone adjustment device of claim 1, wherein the second side surface opposite the elongated slot formed in the first side surface is solid.

3. The reconfigurable bone adjustment device of claim 1, wherein the threaded block includes a first end and a second end, the first end being at least partially disposed in the elongated slot, the first end of the threaded block being welded to the first member.

4. The reconfigurable bone adjustment device of claim 3, wherein the second end of the threaded block is completely devoid of any welding to the first member.

5. The reconfigurable bone adjustment device of claim 3, wherein the first end of the threaded block is welded to the first member via a weld that completely surrounds the first end of the threaded block.

6. The reconfigurable bone adjustment device of claim 3, wherein the second end of the threaded block contacts an inner surface of the second member such that deflection of the threaded block is reduced.

7. The reconfigurable bone adjustment device of claim 1, wherein the slot and the threaded block include a wedge or taper shape.

8. The reconfigurable bone adjustment device of claim 1, wherein the threaded block includes first and second, non-parallel side surfaces.

9. The reconfigurable bone adjustment device of claim 8, wherein the elongated slot defines first and second walls in the second member, the first and second wall being non-parallel relative to each other.

10. A reconfigurable bone adjustment device comprising:
a first member configured for attachment to a first bone fragment;
a second member configured for attachment to a second bone fragment, the second member including an elongated slot;
a drive mechanism configured to move the second member relative to the first member;
a threaded block fixedly coupled to the first member, the threaded block positioned within the elongated slot; and
a threaded rod having a proximal end operatively coupled to the drive mechanism, an intermediate portion threadably coupled to the threaded block, and a distal end operatively coupled to the second member so that rotation of the drive mechanism rotates the threaded rod and moves the second member relative to the first member;
wherein the elongated slot formed in the second member is a thru slot extending from a first circumferential surface of the second member to a second, diametrically opposed circumferential surface of the second member, the thru-slot having an asymmetric design; and
wherein a portion of a circumferential outer surface of the first member positioned between the threaded block and a distal end of the first member is devoid of any slot.

11. The reconfigurable bone adjustment device of claim 10, wherein a width of the slot in the first circumferential surface is greater than a width of the slot in the second circumferential surface.

12. The reconfigurable bone adjustment device of claim 11, wherein the width of the slot in the first circumferential surface is 3 mm and the width of the slot in the second circumferential surface is 1½ mm.

* * * * *